(12) United States Patent
Chang et al.

(10) Patent No.: US 8,851,286 B2
(45) Date of Patent: Oct. 7, 2014

(54) DUAL STERILIZATION CONTAINMENT VESSEL

(71) Applicant: Boston Scientific Scimed, Inc., Maple Grove, MN (US)

(72) Inventors: Robert T. Chang, Belmont, CA (US); Brian K. McCollum, Redwood City, CA (US); Michael J. Conroy, Cupertino, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 148 days.

(21) Appl. No.: 13/676,695

(22) Filed: Nov. 14, 2012

(65) Prior Publication Data
US 2013/0118949 A1 May 16, 2013

Related U.S. Application Data

(60) Provisional application No. 61/559,914, filed on Nov. 15, 2011.

(51) Int. Cl.
| | |
|---|---|
| *A61F 2/24* | (2006.01) |
| *A61F 2/00* | (2006.01) |
| *A61L 2/00* | (2006.01) |
| *A61L 2/26* | (2006.01) |

(52) U.S. Cl.
CPC .............. *A61L 2/26* (2013.01); *A61F 2/0095* (2013.01); *A61L 2/0088* (2013.01); *A61F 2/2436* (2013.01); *A61L 2/0029* (2013.01); *A61L 2202/21* (2013.01)
USPC .............................. 206/464; 206/438; 623/2.1

(58) Field of Classification Search
USPC ................... 206/363, 364, 438; 623/2.1, 2.11
See application file for complete search history.

(56) References Cited

U.S. PATENT DOCUMENTS

| | | | |
|---|---|---|---|
| 6,416,547 B1 * | 7/2002 | Erickson et al. ............. | 623/2.11 |
| 7,318,278 B2 | 1/2008 | Zhang et al. | |
| 7,329,279 B2 | 2/2008 | Haug et al. | |
| 7,381,219 B2 | 6/2008 | Salahieh et al. | |
| 7,389,874 B2 * | 6/2008 | Quest et al. .................... | 206/438 |
| 7,445,631 B2 | 11/2008 | Salahieh et al. | |
| 7,699,168 B2 * | 4/2010 | Ryan et al. .................... | 206/438 |
| 7,712,606 B2 | 5/2010 | Salahieh et al. | |
| 7,748,389 B2 | 7/2010 | Salahieh et al. | |
| 7,824,442 B2 | 11/2010 | Salahieh et al. | |
| 7,824,443 B2 | 11/2010 | Salahieh et al. | |
| 7,959,666 B2 | 6/2011 | Salahieh et al. | |
| 7,959,672 B2 | 6/2011 | Salahieh et al. | |

(Continued)

OTHER PUBLICATIONS

US 8,062,356, 11/2011, Salahieh et al. (withdrawn).

(Continued)

*Primary Examiner* — David Fidei
(74) *Attorney, Agent, or Firm* — Seager, Tufte & Wickhem LLC

(57) ABSTRACT

The disclosure pertains to a vessel for holding replacement heart valves and associated positioning and installation apparatus which is configured and adapted to contain a biocidal sterilization fluid during and following exposure of a delivery system for the replacement heart valve to sterilization by ionizing radiation and methods of use therefor. The vessel includes a shield which limits exposure of biologically derived material therein to radiation. The vessel also provides a storage and shipping container for the replacement heart valve in which the biologically derived material is maintained in a sterile fluid environment.

20 Claims, 6 Drawing Sheets

(56) References Cited

U.S. PATENT DOCUMENTS

| | | |
|---|---|---|
| 7,967,138 B2 | 6/2011 | Ryan et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,182,528 B2 | 5/2012 | Salahieh |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,328,868 B2 | 12/2012 | Paul et al. |
| 8,343,213 B2 | 1/2013 | Salahieh et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2007/0061008 A1 | 3/2007 | Salahieh et al. |
| 2007/0162107 A1 | 7/2007 | Haug et al. |
| 2008/0010947 A1 | 1/2008 | Huang et al. |
| 2008/0125859 A1 | 5/2008 | Salahieh et al. |
| 2008/0234814 A1 | 9/2008 | Salahieh et al. |
| 2009/0008279 A1 * | 1/2009 | Tanghoej ............... 206/364 |
| 2010/0219092 A1 | 9/2010 | Salahieh et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0252470 A1 | 10/2010 | Ryan et al. |
| 2010/0256749 A1 | 10/2010 | Tran et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0290079 A1 * | 11/2012 | Murad et al. ............. 623/2.17 |
| 2012/0330409 A1 | 12/2012 | Haug et al. |

OTHER PUBLICATIONS

US 8,062,357, 11/2011, Salahieh et al. (withdrawn).
US 8,075,614, 12/2011, Salahieh et al. (withdrawn).
US 8,133,271, 03/2012, Salahieh et al. (withdrawn).
US 8,211,170, 07/2012, Paul et al. (withdrawn).

* cited by examiner

US 8,851,286 B2

DUAL STERILIZATION CONTAINMENT VESSEL

TECHNICAL FIELD

The present disclosure pertains to medical devices, and methods for manufacturing medical devices. More particularly, the present disclosure pertains to medical devices for delivering a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure pertains to a sealable dual sterilization containment vessel for biologically derived medical components comprising a hollow element having a wall, a proximal end, a distal end, and a lumen therebetween, said lumen configured and adapted to contain a biologically derived medical component and at least a portion of an apparatus configured and adapted to implant the biologically derived medical component in a living body; a distal end cap; a proximal end cap; and a radiopaque sleeve, wherein the proximal end cap has a secondary proximal end cap and ferrule sized and adapted to and capable of reversibly sealing the proximal end cap to a delivery catheter passing therethrough, further wherein the combination of the hollow element, the distal end cap, the proximal end cap, the secondary proximal end cap, the ferrule, and the delivery catheter form a fluid tight system providing a continuous fluid connection between the interior of the hollow element and the lumen of the delivery catheter.

In another embodiment, the disclosure relates to a sealed system for delivering a replacement heart valve comprising a replacement heart valve; a delivery catheter; and elements configured and adapted to position and install the replacement heart valve; the system further comprising a storage and shipping container, wherein at least the replacement heart valve and a portion of the elements configured and adapted to position and install the replacement heart valve are initially contained within a fluid filled removable dual sterilization containment vessel. The biologically derived component(s) of the replacement heart valve may be maintained in a hydrated state within the provided sterile system environment during storage and shipping.

DETAILED DESCRIPTION

Figure 1:
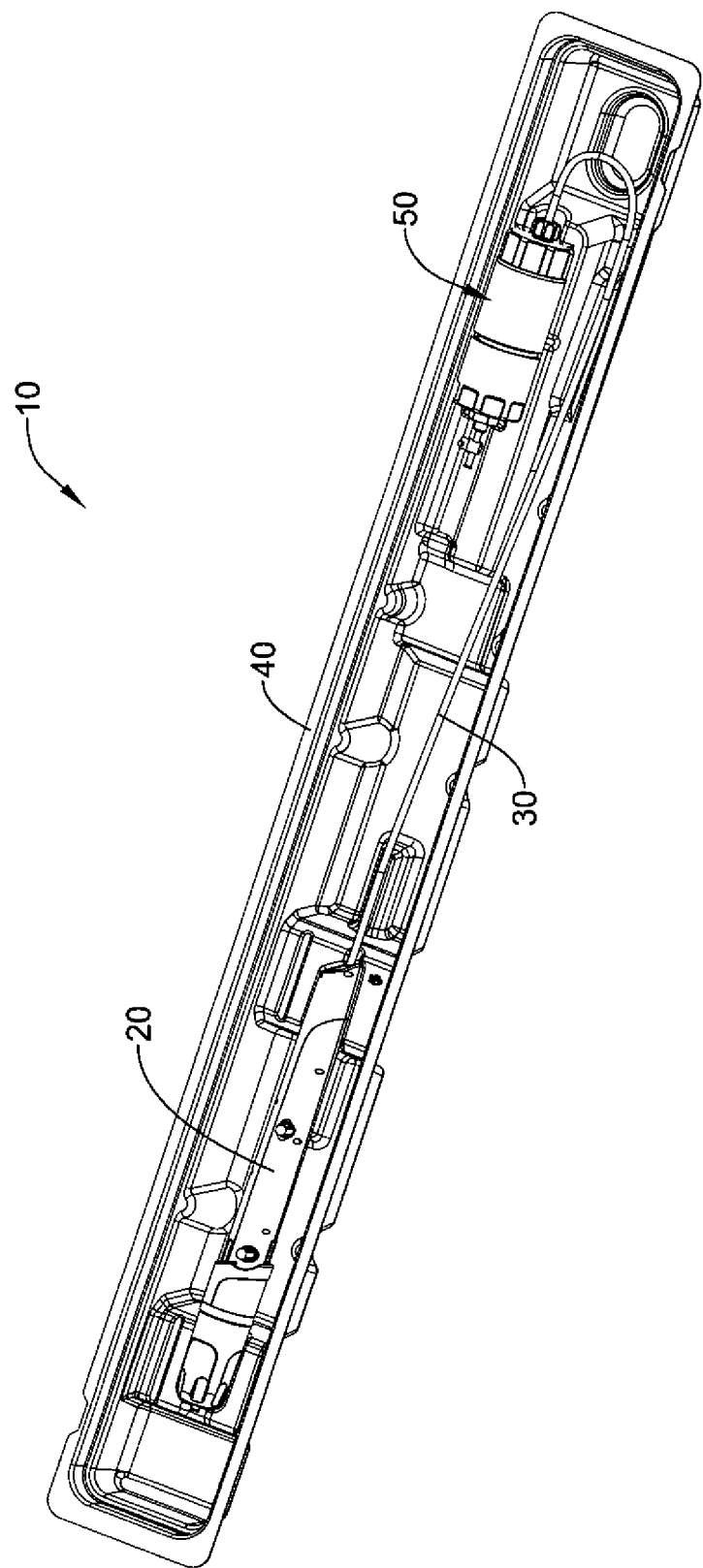
FIG. 1 illustrates an exemplary replacement heart valve delivery system and associated packaging.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described unless clearly stated to the contrary.

Figure 2:
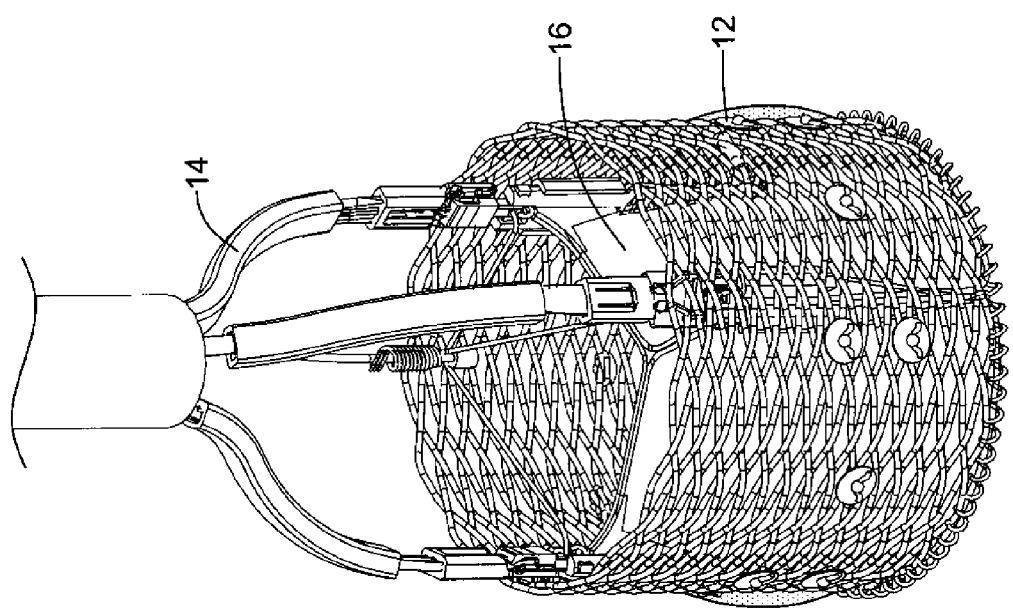
FIG. 2 illustrates a replacement heart valve and associated components which may be used with the dual sterilization containment vessel disclosed herein

FIG. 1 illustrates a system 10 for delivering a replacement heart valve and packaging 40 associated therewith. The heart valve replacement system 10 may comprise a replacement heart valve 12, having a biologically derived component 16, and associated components 14 (FIG. 2) configured and adapted to position and install the replacement heart valve 12. These components may be any of the replacement heart valves and associated components known in the art and the specifics thereof need not be discussed in detail to understand the operation of the system. The non-limiting exemplary replacement heart valve 12 may be a valve including one or more biologically derived components and may, for example, be derived from treated human, bovine, or porcine tissue. The system 10 for delivering a replacement heart valve also may include additional components such as a control handle 20, a delivery catheter 30 and a dual sterilization containment vessel 50 which is configured and adapted to contain at least one biocidal fluid (not shown), which biocidal fluid may also be contained within the delivery catheter 20 and in fluid contact therewith. The biocidal fluid may contain, for example, gluteraldehyde which serves to sterilize the contacted surfaces of the system and which optionally may tend to cross-link biologically derived components of the replacement heart valve.

Figure 3:
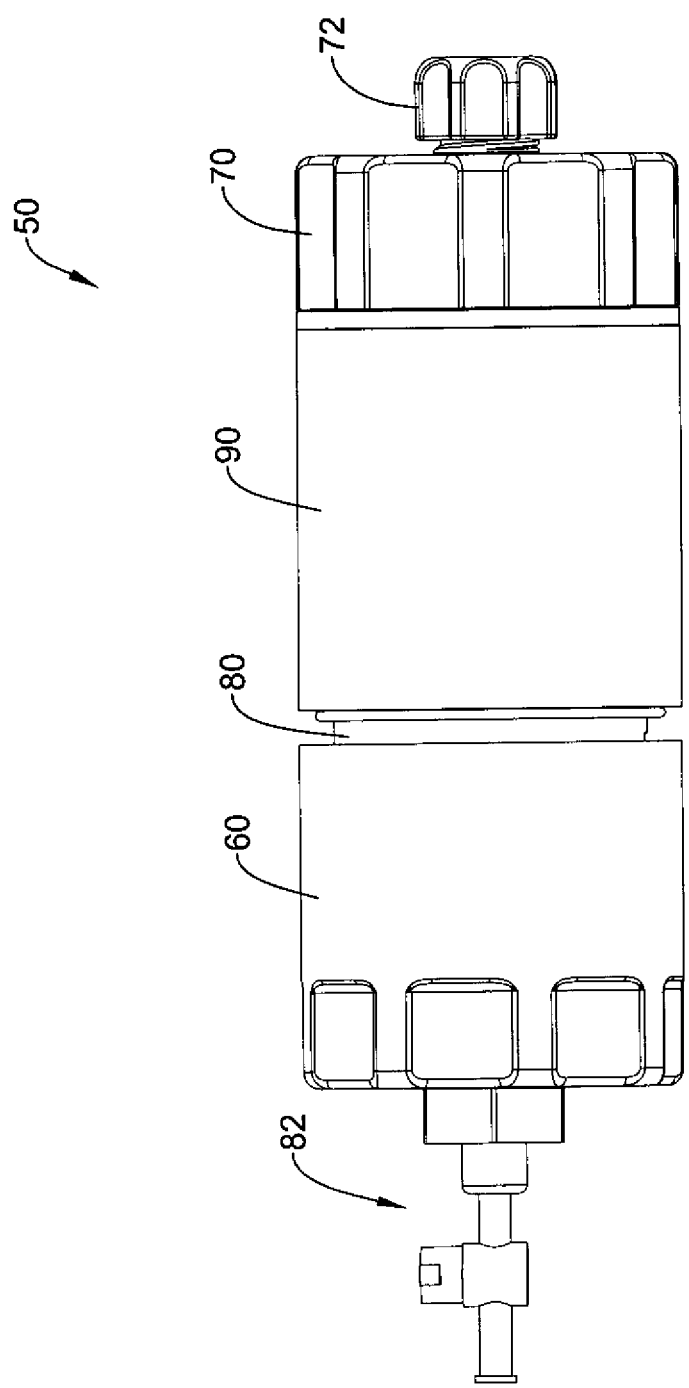
FIG. 3 illustrates a dual sterilization containment vessel of the disclosure.
Figure 4A:
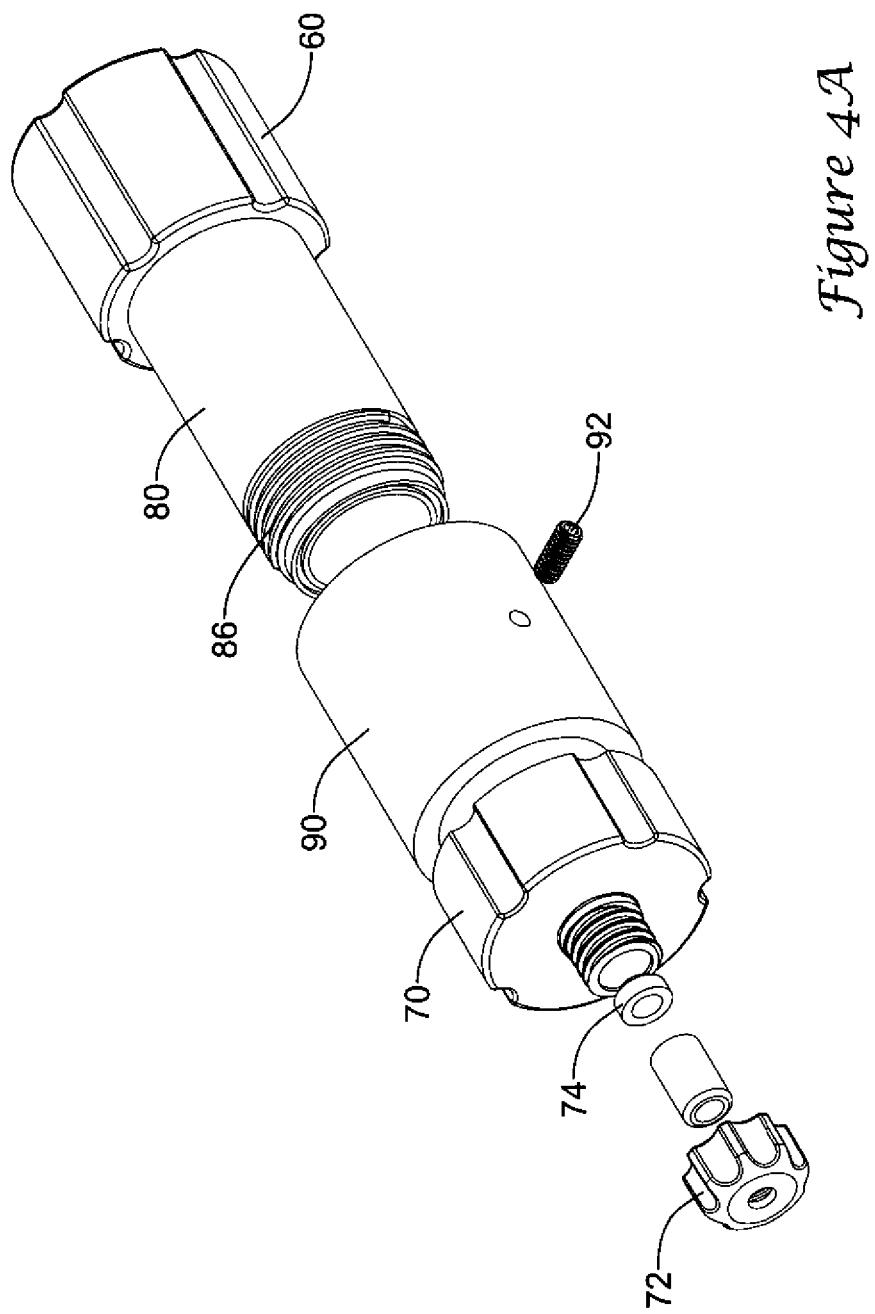
FIGS. 4A and 4B illustrate partially exploded views of the dual sterilization containment vessel of FIG. 3.
Figure 4B:
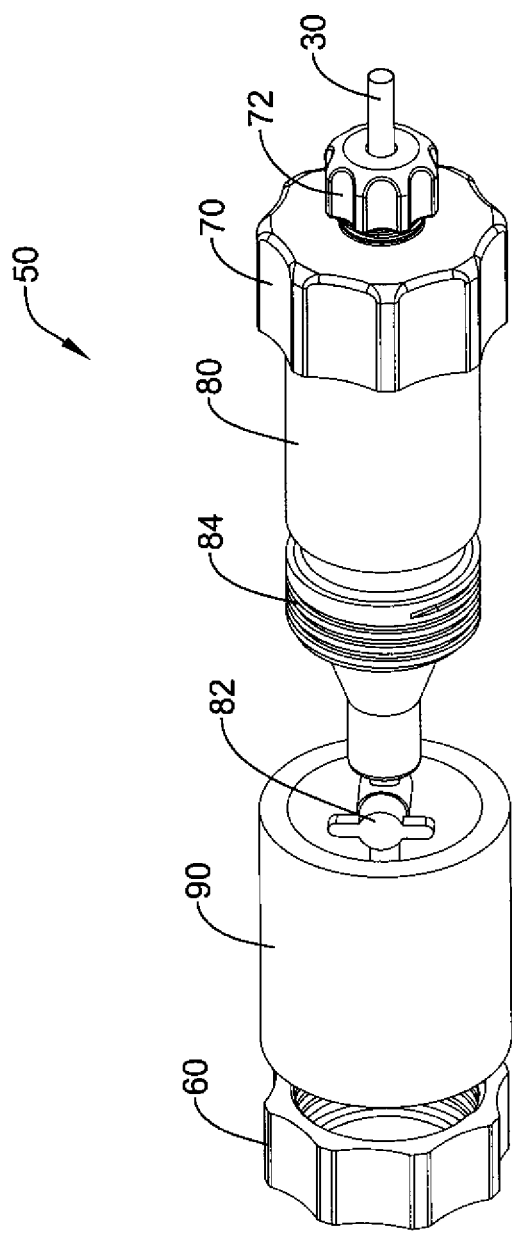

FIGS. 3, 4A, and 4B illustrate various components of a dual sterilization containment vessel 50 which is configured and adapted to contain at least one biocidal fluid. A dual sterilization containment vessel 50 will be understood to encompass a vessel which is configured and adapted to contain at least one sterilizing biocidal fluid as well as to allow ionizing radiation sterilization of the contents of the vessel and other components of a replacement heart valve delivery system without undue damage to the biologically derived components 16 of the replacement heart valve 12.

In some embodiments, this may be accomplished by selecting construction materials which are substantially unreactive with the contacting biocide(s) and further by including as a component the dual sterilization containment vessel 50 a radiopaque sleeve 90 which prevents excessive levels of ionizing radiation which may be applied to the remaining components of the system 10 for delivering a replacement heart valve from reaching and damaging the biologically derived components. The radiopaque sleeve 90 may be removable or may be permanently attached to one or more other components of the dual sterilization containment vessel 50. In certain embodiments, the radiopaque sleeve 90 may be contained within the sterilization containment vessel 50 to ensure that the space between an external radiopaque sleeve 90 and the sterilization containment vessel 50 remains sterile. In certain other embodiments, the joins between an external radiopaque sleeve 90 and the sterilization containment vessel 50 may be sealed, for example by an O-ring, gasket, sealant, or the like to isolate the space between an external radiopaque sleeve 90 and the sterilization containment vessel 50 and maintain a sterile environment therebetween. In yet other embodiments, the external radiopaque sleeve 90 and the sterilization containment vessel 50 may be integrally formed to eliminate an exposed interface which might harbor contamination.

The use of a dual sterilization containment vessel 50 is particularly desirable when other components of the system 10 for delivering a replacement heart valve 12 require exposure of the system as a whole to high levels of ionizing radiation to ensure that biocidal dosage levels are delivered to all internal parts of the system. Further, the use of two separate sterilization methods, enabled by the presence of a dual sterilization containment vessel 50 within the system is believed to substantially reduce the risk of bioactive contamination.

FIGS. 3, 4A, and 4B illustrate a hollow element 80 having a wall, a proximal end, a distal end, and a lumen therebetween, said lumen configured and adapted to contain a biologically derived medical component 16 and at least a portion of an apparatus 14 configured and adapted to position and implant the biologically derived medical component 16 in a living body; a distal end cap 60; a proximal end cap 70 wherein the proximal end cap 70 has a secondary proximal end cap 72 and ferrule 74 sized and adapted to and capable of reversibly sealing the proximal end cap 70 to a delivery catheter 30 passing therethrough. Further, the combination of the hollow element 80, the distal end cap 60, the proximal end cap 70, the secondary proximal end cap 72, the ferrule 74, delivery catheter 30, and handle 20 form a fluid tight system providing a continuous fluid connection between the interior of the hollow element 80 and the lumen of the delivery catheter 30. In some embodiments, the hollow element 80, and/or the distal end cap 60, may include a stopcock 82 to facilitate filling and draining biocide (s) from the system prior to removal of the dual sterilization containment vessel 50.

Figure 5:
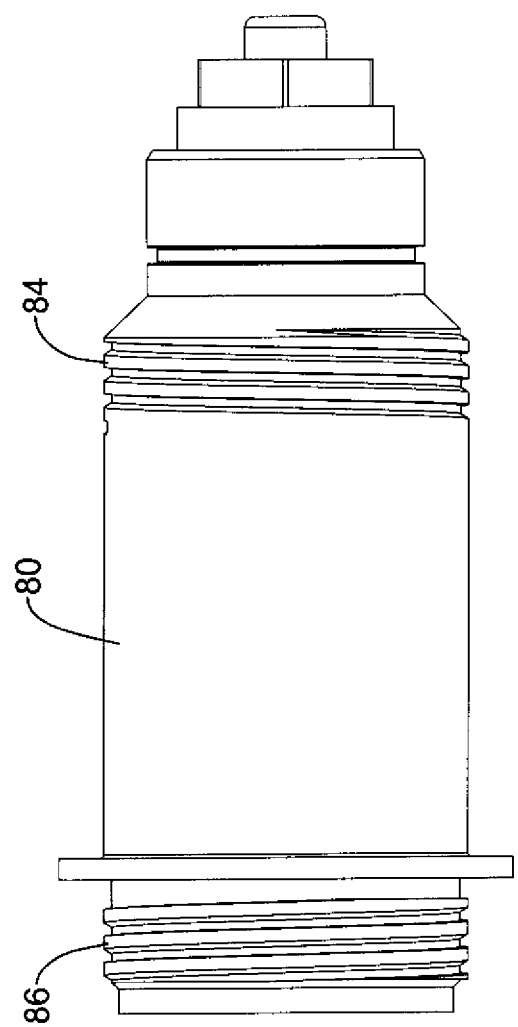
FIG. 5 illustrates an embodiment of a hollow element of an embodiment of the disclosure.

Hollow element 80, illustrated in greater detail in FIG. 5, comprises a hollow body having sufficient internal volume to contain the replacement heart valve and at least a portion of the associated components 14 configured and adapted to position and install the replacement heart valve 12. In some embodiments, the replacement heart valve 12 and associated components 14 configured and adapted to position and install the replacement heart valve 12 are stored in at least a somewhat expanded configuration which may more fully expose their components to the biocidal fluid contained therein. Although illustrated as generally cylindrical, it will be appreciated the hollow element 80 may have a rectangular or other cross-section if desired. Hollow element 80 is depicted as having a unitary construction, however in some embodiments the hollow body may be fabricated in two or more segments which are suitably sealed when joined. For example, the hollow body may be formed from two half-cylindrical walls joined along a separable longitudinal seam, such as a clam-shell arrangement, with an appropriate gasket therebetween. In some embodiments, hollow body 80 may include stopcock 82.

As noted herein, construction materials which are substantially unreactive with the contacting biocide(s), such as polycarbonate, may be used for the hollow element 80 and other components of the dual sterilization containment vessel 50. Such materials may be selected to be partially or fully transparent to visible light thereby allowing visual inspection of the contents. In addition, the materials should remain substantially unchanged chemically and mechanically upon absorption of ionizing radiation at levels of 30, 40, 50 gray, or in some embodiments more whether empty or filled with a biocidal fluid. In certain embodiments, at least a portion of the interior of at least one of the hollow element 80, the distal cap 60, and the proximal cap 70 may include a polished surface in fluid communication with the interior of the hollow element which is believed to facilitate removal of bubbles from the biocidal fluid within the dual sterilization containment vessel 50. In addition, hollow element 80 may include one or more features configured and adapted to direct the motion of any bubbles which may be present within the dual sterilization containment vessel 50 when it is filled with fluid and subject to changes in orientation. Such features may include ridges, grooves, and/or tapers.

As illustrated, distal cap 60 and proximal cap 70 may be secured to hollow element 80 by mating threaded sections. Other means of reversible attachment may also be used. Although the illustrated embodiment depicts male threads 84, 86 on the hollow body 80 and corresponding female threads on the end caps 60, 70, it will be appreciated that a cap may be provided with male threads and the hollow body with female threads at one or both ends of the dual sterilization containment vessel 50.

Proximal end cap 70 may include a secondary proximal end cap 72 which together with ferrule 74 acts to seal the dual sterilization containment vessel 50 to other parts, indicated by reference numeral 30, of the illustrated system 10 for delivering a replacement heart valve 12 while maintaining a fluid connection with the lumen or lumens thereof.

Removable radiopaque sleeve 90 will typically have an internal lumen which substantially matches the exterior shape and dimension of the hollow element 80. The radiopaque sleeve 90 may comprise a radiopaque solid or a radiopaque fluid or gel. Radiopaque sleeve 90 optionally may be secured to the hollow element 80 by, for example, set screw 92 during a portion of the sterilization process. In the alternative, the radiopaque sleeve may be formed from several pieces and held in place by a clamping element (not shown). In such embodiments, the pieces may include overlapping regions along the joins to ensure that higher than desirable ionizing radiation does not reach biologically derived components 16. In yet other embodiments, the radiopaque sleeve 90 may be permanently attached to one or more of the other components of dual sterilization containment vessel 50. The radiopacity of the combined radiopaque sleeve 90 may be selected such that in combination with hollow body 80, the biologically derived medical component 16 absorbs no more than 4 gray when the dual sterilization containment vessel 50 absorbs 30, 40, 50 gray, or in some embodiments more whether the dual sterilization containment vessel 50 is empty or filled with a biocidal fluid.

Although one or both of distal cap 60 and proximal cap 70 may be sized and configured to retain radiopaque sleeve 90 in position about hollow element 80, it will be appreciated that in some embodiments, the radiopaque sleeve 90 may be configured to be removable from the hollow element 80 without removing one or both of the end caps. In such embodiments, a set screw 94 or other retaining device may be employed.

One possible, non-limiting, use sequence for a dual sterilization containment vessel 50 may be described as follows. Replacement heart valve 12 and associated components 14 configured and adapted to position and install the replacement heart valve 12 may be withdrawn within delivery catheter 30, whereupon an assembled dual sterilization containment vessel 50 may be positioned to partially encompass the distal end of the delivery catheter 30. Once proximal end cap 70 is secured to the distal end of delivery catheter 30 by secondary proximal end cap 72 and ferrule 74, replacement heart valve 10 and associated components 14 configured and adapted to position and install the replacement heart valve 12 may be advanced from the distal end of delivery catheter 30 until it achieves an expanded configuration such as that of FIG. 2. Continuous lumen(s) joining handle 20, delivery catheter 30, and dual sterilization containment vessel 50 may then be filled with a biocidal fluid, such as an alcoholic gluteraldehyde solution, and flushed to remove bubbles and any incidentally introduced debris. Following flushing, stopcock 82 and a corresponding stopcock associated with handle 20 may be closed to seal and contain the biocidal fluid within the now closed system.

The closed system may be placed in packaging 40 and exposed to a source of ionizing radiation of sufficient penetrating power and for a sufficient time to sterilize the contents of packaging 40. Radiopaque sleeve 90 serves to limit the radiation absorbed by the biologically derived component(s) 16. In some embodiments, the radiation absorbed by biologically derived component(s) 16 will be less than 4 gray when the system as a whole has absorbed 30, 40, 50 gray, or in some embodiments more. At this point, it will be appreciated that the contents of the system have been sterilized by two independent methods and is ready for storage and distribution prior to use in a heart valve replacement procedure. The dual sterilization containment vessel 50 is configured and adapted to maintain the biologically derived medical component(s) in a hydrating and sterile environment prior to use.

Although the illustrative examples described herein relate to replacement heart valves, use of the dual sterilization containment vessel with other biologically derived medical components is also contemplated. In such an embodiment, the biologically derived medical component may be present in the form of a different valve structure, stent graft, or the like. Dual sterilization containment vessels for such applications may require modifications in size, shape and/or materials.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A dual sterilization containment vessel for biologically derived medical components comprising:
   a hollow element having a wall, a proximal end, a distal end, and a lumen therebetween, said lumen configured and adapted to contain a biologically derived medical component and at least a portion of an apparatus configured and adapted to implant the biologically derived medical component in a living body;
   a distal end cap;
   a proximal end cap; and
   a radiopaque sleeve,
   wherein the proximal end cap has a secondary proximal end cap and ferrule sized and adapted to and capable of reversibly sealing the proximal end cap to a delivery catheter passing therethrough,
   further wherein the combination of the hollow element, the distal end cap, the proximal end cap, the secondary proximal end cap, the ferrule, and the delivery catheter form a fluid tight system providing a continuous fluid connection between the interior of the hollow element and the lumen of the delivery catheter.

2. The dual sterilization containment vessel of claim 1, where in the hollow element, the distal cap, and the proximal cap comprise a material substantially unreactive with at least one biocide.

3. The dual sterilization containment vessel of claim 1, wherein the hollow element, the distal cap, and the proximal cap comprise a material which is substantially unchanged chemically and mechanically upon absorption of at least 4 gray of ionizing radiation.

4. The dual sterilization containment vessel of claim 1, wherein the hollow element, the distal cap, and the proximal cap comprise a material which is substantially unchanged chemically and mechanically upon absorption of at least 30 gray of ionizing radiation.

5. The dual sterilization containment vessel of claim 1, wherein the hollow element, the distal cap, and the proximal cap comprise a material which is substantially unchanged chemically and mechanically upon absorption of at least 40 gray of ionizing radiation.

6. The dual sterilization containment vessel of claim 1, wherein the hollow element, the distal cap, and the proximal cap comprise a material which is substantially unchanged chemically and mechanically upon absorption of at least 50 gray of ionizing radiation.

7. The dual sterilization containment vessel of claim 1, wherein the hollow element, the distal cap, and the proximal cap comprise a material which is substantially unchanged chemically and mechanically upon absorption of at least 4 gray of ionizing radiation when filled with the biocide of claim 2.

8. The dual sterilization containment vessel of claim 1, wherein the hollow element, the distal cap, and the proximal cap comprise a material which is substantially unchanged chemically and mechanically upon absorption of at least 30 gray of ionizing radiation when filled with the biocide of claim 2.

9. The dual sterilization containment vessel of claim 1, wherein the hollow element, the distal cap, and the proximal cap comprise a material which is substantially unchanged chemically and mechanically upon absorption of at least 40 gray of ionizing radiation when filled with the biocide of claim 2.

10. The dual sterilization containment vessel of claim 1, wherein the hollow element, the distal cap, and the proximal cap comprise a material which is substantially unchanged chemically and mechanically upon absorption of at least 50 gray of ionizing radiation when filled with the biocide of claim 2.

11. The dual sterilization containment vessel of claim 5, wherein the biologically derived medical component receives at least 4 gray of ionizing radiation when the hollow element absorbs 30 gray of ionizing radiation.

12. The dual sterilization containment vessel of claim 5, wherein the biologically derived medical component receives at least 4 gray of ionizing radiation when the hollow element absorbs 40 gray of ionizing radiation.

13. The dual sterilization containment vessel of claim 5, wherein the biologically derived medical component receives at least 4 gray of ionizing radiation when the hollow element absorbs 50 gray of ionizing radiation.

14. The dual sterilization containment vessel of claim 11, wherein the biologically derived medical component is treated bovine tissue.

15. The dual sterilization containment vessel of claim 14, wherein the biologically derived medical component is a replacement valve.

16. The dual sterilization containment vessel of claim 15, wherein the replacement valve is a replacement heart valve.

17. The dual sterilization containment vessel of claim 11, wherein the biologically derived medical component is treated porcine tissue.

18. The dual sterilization containment vessel of claim 17, wherein the biologically derived medical component is a replacement valve.

19. The dual sterilization containment vessel of claim 18, wherein the replacement valve is a replacement heart valve.

20. The dual sterilization containment vessel of claim 1, wherein at least a portion of at least one of the hollow element, the distal cap, and the proximal cap includes a region transparent to visible light.

* * * * *